United States Patent
Sugimoto (10) Patent No.: US 8,472,014 B2
(45) Date of Patent: Jun. 25, 2013

(54) REFRACTIVE INDEX DISTRIBUTION MEASURING METHOD AND REFRACTIVE INDEX DISTRIBUTION MEASURING APPARATUS

(75) Inventor: Tomohiro Sugimoto, Yoshikawa (JP)

(73) Assignee: Canon Kabushiki Kaisha (JP)

( * ) Notice: Subject to any disclaimer, the term of this patent is extended or adjusted under 35 U.S.C. 154(b) by 0 days.

(21) Appl. No.: 13/511,460

(22) PCT Filed: May 19, 2011

(86) PCT No.: PCT/JP2011/062041
§ 371 (c)(1),
(2), (4) Date: May 23, 2012

(87) PCT Pub. No.: WO2011/149000
PCT Pub. Date: Dec. 1, 2011

(65) Prior Publication Data
US 2012/0241989 A1    Sep. 27, 2012

(30) Foreign Application Priority Data
May 25, 2010    (JP) ................. 2010-119558

(51) Int. Cl.
*G01N 21/41*    (2006.01)
*G01B 9/00*    (2006.01)

(52) U.S. Cl.
USPC .......................................... 356/128; 356/124

(58) Field of Classification Search
None
See application file for complete search history.

(56) References Cited

U.S. PATENT DOCUMENTS

| 4,265,534 A | 5/1981 | Remijan |
| 4,541,697 A | 9/1985 | Remijan |
| 4,542,989 A | 9/1985 | Remijan |

(Continued)

FOREIGN PATENT DOCUMENTS

| JP | 58045526 A | 3/1983 |
| JP | 61-070436 A | 4/1986 |

(Continued)

OTHER PUBLICATIONS

Ranjbar, et al., "Nondestructive Measurement of Refractive Index Profile of Optical Fiber Preforms Using Moire Technique and Phase Shift Method", Optical Communication, vol. 6025, 602520, 2006 (Cited in PCT/JP2011/062041 ISR Aug. 30, 2011).

(Continued)

*Primary Examiner* — Gregory J Toatley
*Assistant Examiner* — Shawn Decenzo
(74) *Attorney, Agent, or Firm* — Rossi, Kimms & McDowell LLP (57) ABSTRACT

A method includes measuring a transmitted wavefront of a test object by introducing reference light into the test object arranged in a medium having a refractive index different from a refractive index of the test object, and calculating a refractive index distribution of the test object by using a measurement result of the transmitted wavefront. The measuring step measures a first transmitted wavefront for a first wavelength and a second transmitted wavefront for a second wavelength different from the first wavelength. The calculating step calculates the refractive index distribution of the test object by removing a shape component of the test object utilizing measurement results of the first and the second transmitted wavefront, and a transmitted wavefront of a reference object arranged in the medium for each of the first and second wavelengths. The reference object has the same shape as the test object and a specific refractive index distribution.

7 Claims, 4 Drawing Sheets

U.S. PATENT DOCUMENTS

| | | | |
|---|---|---|---|
| 4,565,449 A * | 1/1986 | Grego | 356/484 |
| 4,744,654 A | 5/1988 | Jinno et al. | |
| 4,934,818 A | 6/1990 | Glantschnig et al. | |
| 5,151,752 A * | 9/1992 | Oono et al. | 356/128 |
| 5,309,214 A * | 5/1994 | Hashimoto | 356/128 |
| 5,526,118 A * | 6/1996 | Miyagawa et al. | 356/484 |
| 6,765,661 B2 | 7/2004 | Biel et al. | |
| 7,388,676 B2 * | 6/2008 | Sawada | 356/517 |
| 2006/0159332 A1 | 7/2006 | Sawada | |
| 2007/0109555 A1 | 5/2007 | Gustafsson et al. | |
| 2009/0109401 A1 * | 4/2009 | Van Heugten | 351/221 |
| 2009/0147241 A1 | 6/2009 | Shlezinger et al. | |
| 2010/0165355 A1 | 7/2010 | Kato | |
| 2010/0245842 A1 | 9/2010 | Kato | |
| 2011/0134438 A1 * | 6/2011 | Kato | 356/517 |
| 2011/0292379 A1 | 12/2011 | Kato | |
| 2012/0139136 A1 | 6/2012 | Kato | |
| 2012/0241989 A1 * | 9/2012 | Sugimoto | 264/1.1 |

FOREIGN PATENT DOCUMENTS

| | | | |
|---|---|---|---|
| JP | 1-35282 B2 | | 7/1989 |
| JP | 1316627 A | | 12/1989 |
| JP | 02-008726 A | | 1/1990 |
| JP | 02008726 A | | 1/1990 |
| JP | 3128411 A | | 5/1991 |
| JP | 03-225259 A | | 10/1991 |
| JP | 08-014852 A | | 1/1996 |
| JP | 08-304229 A | | 11/1996 |
| JP | 11-044641 A | | 2/1999 |
| JP | 2005-106835 A | | 4/2005 |
| JP | 2005-201724 A | | 7/2005 |
| JP | 2006-200999 A | | 8/2006 |
| JP | 2010-151578 A | | 7/2010 |

OTHER PUBLICATIONS

International Search Report issued Aug. 30, 2011 for parent PCT/JP2011/062041.

Korean Office Action for KR 10-2009-012038, dated Aug. 10, 2012. Cited in related US 2010/0245842.

Takeda, Mitsuo et al. "Lateral aberration measurements with a digital Talbot interferometer," Applied Optics, vol. 23, No. 11, Jun. 1, 1984, pp. 1760-1764. Cited in related US 2010/0245842.

Takeda, Mitsuo et al. "Fourier-transform method of fringe-pattern analysis for computer-based topography and interferometry," Optical Society of America, Vo. 72, No. 1, Jan. 1982, pp. 156-160. Cited in related US 201010245842.

* cited by examiner

REFRACTIVE INDEX DISTRIBUTION MEASURING METHOD AND REFRACTIVE INDEX DISTRIBUTION MEASURING APPARATUS

This application is a U.S. National Phase Application of PCT International Application PCT/JP2011/062041 filed on May 19, 2011 which is based on and claims priority from JP 2010-119558 filed on May 25, 2010 the contents of which is incorporated herein in its entirety by reference.

TECHNICAL FIELD

The present invention relates to a refractive index distribution measuring method and a refractive index distribution measuring apparatus.

BACKGROUND ART

Japanese Patent Laid-Open No. ("JP") 08-014852 proposes a method for finding a refractive index distribution of a flat-shaped test object using two beams having different wavelengths. JP 02-008726 proposes a method for finding a refractive index distribution of a test object by measuring a transmitted wavefront while the test object is immersed in each of two types of matching oils each having a slightly different refractive index from that of the test object.

The method disclosed in JP 08-014852 requires working of the test object into the flat shape. The working of the test object is time-consuming, and changes the internal stress of the test object and thus its internal refractive index distribution before and after the working, thereby causing a refractive index distribution to be different from the pre-working refractive index distribution.

The method disclosed in JP 02-008726 requires preparing two types of matching oils having refractive indices approximately equal to the refractive index of the test object. An adjustment of the refractive index of the matching oil requires a blend of different types of oils and this adjustment is time-consuming. In addition, the matching oil having a high refractive index provides a low transmittance. Therefore, when the transmitted wavefront of the test object having a high refractive index is measured in accordance with the method of JP 02-008726, a detector can output only a weak signal, deteriorating the measuring precision of the test object.

SUMMARY OF INVENTION

The present invention provides a refractive index distribution measuring method and a refractive index distribution measuring apparatus, which can quickly and highly precisely measure a refractive index distribution of a test object in a nondestructive state.

A refractive index distribution measuring method according to the present invention includes the steps of measuring a transmitted wavefront of a test object by introducing reference light into the test object that is arranged in a medium having a refractive index different from a refractive index of the test object, and calculating a refractive index distribution of the test object by using a measurement result of the transmitted wavefront. The measuring step measures a first transmitted wavefront for a first wavelength and a second transmitted wavefront for a second wavelength different from the first wavelength. The calculating step calculates the refractive index distribution of the test object by removing a shape component of the test object utilizing measurement results of the first and the second transmitted wavefront, and a transmitted wavefront of a reference object arranged in the medium for each of the first and second wavelengths. The reference object has the same shape as the test object and a specific refractive index distribution.

Further features and aspects of the present invention will become apparent from the following description of exemplary embodiments with reference to the attached drawings.

DESCRIPTION OF EMBODIMENTS

Exemplary embodiments of the present invention will be described below with reference to the accompanied drawings.

First Embodiment

A description will now be given of a refractive index distribution measuring apparatus that executes a refractive index distribution measuring method according to a first embodiment. The refractive index distribution measuring apparatus measures a transmitted wavefront of a test object by immersing the object in a medium (M) having a refractive index different from that of the test object and by introducing two types of reference beams, such as light of a first wavelength and light of a second wavelength, into the object. The refractive index distribution measuring apparatus then calculates a refractive index distribution of the test object utilizing a measurement result of the transmitted wavefront. The test object is a lens (optical element) having a positive power.

Figure 1A:
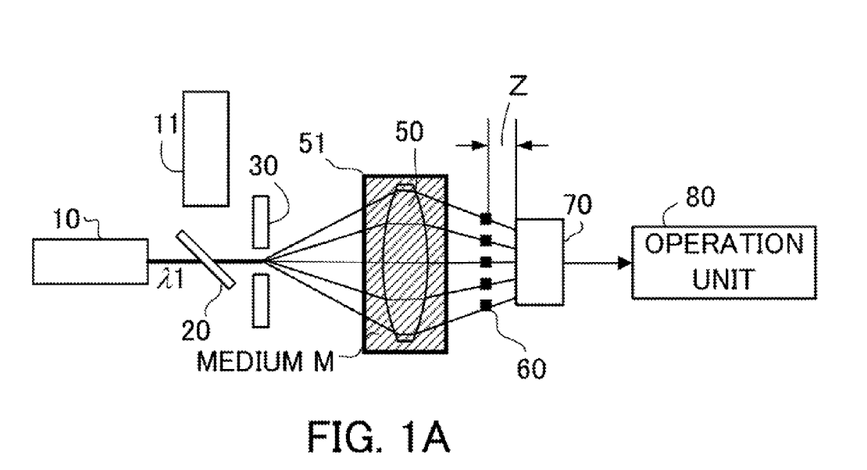
FIGS. 1A and 1B are block diagrams of a refractive index distribution measuring apparatus according to a first embodiment.
Figure 1B:
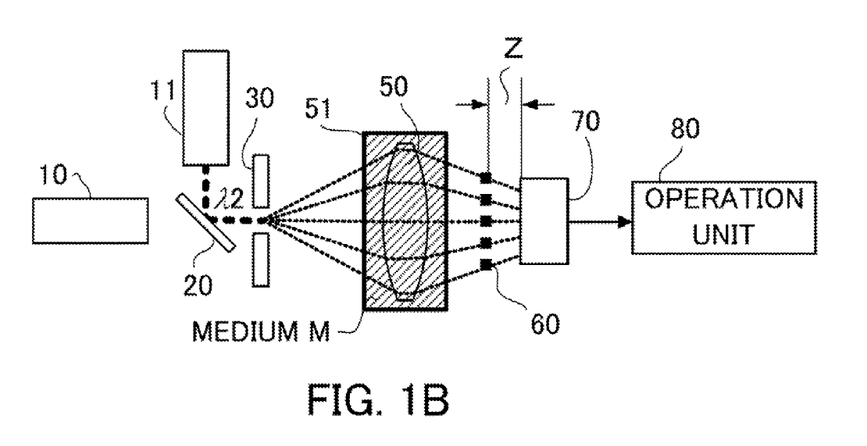

FIG. 1 is a block diagram of a Talbot interferometer as a measuring unit configured to measure the transmitted wavefront of the test object 50 utilizing two beams having different wavelengths. A side surface of a test object case 51 is made of a light transmitting material, such as glass. The test object case 51 houses a material, such as oil, and the test object 50.

As illustrated in FIG. 1A, light emitted from a (first) light source 10, such as a He—Ne laser, has a first wavelength $\lambda_1$, passes through a beam splitter 20, such as a dichroic mirror, and reaches a pinhole 30 in a pinhole plate. On the other hand, as illustrated in FIG. 1B, light emitted from a (second) light source 11, such as a He—Cd laser, has a second wavelength $\lambda_2$, is reflected on the beam splitter 20, and reaches the pinhole 30. Here, an optical axis direction is set to a direction in which the light is emitted from the light source 10, and an optical axis is set to the center of the light flux.

The light passes the pinhole 30 and is diffracted. A diameter $\Phi$ of the pinhole 30 is so small that the diffracted light can be regarded as an ideal spherical wave and is designed so that the diameter $\Phi$ can be considered to satisfy Expression 1 with a numerical aperture ("NA") on the object side and a wavelength $\lambda$ of the light:

$$\Phi \sim \frac{\lambda}{NA} \qquad \text{Expression 1}$$

Since the wavelength $\lambda_2$ of the He—Cd laser is smaller than the wavelength $\lambda_1$ of the He—Ne laser in this embodiment, the pinhole 30 is formed so that it can satisfy Expression 1 for the wavelength $\lambda_2$. For example, when $\lambda_2$ is 442 nm and NA is about 0.2, the pinhole 30 may have a diameter $\Phi$ of about 2 μm.

The light becomes divergent light after it passes the pinhole 30, enters the test object 50 through the medium M in the test object case 51, becomes convergent light by the positive power of the test object 50 in this embodiment, and passes a two-dimensional orthogonal diffraction grating 60. Then, the light is captured (measured) by the image pickup element 70 as a detector, such as a CCD sensor or a CMOS sensor. When the NA of the transmitted light that has transmitted the test object 50 is small and a distance Z between the diffraction grating 60 and the image pickup element 70 satisfies the Talbot condition provided by Expression 2, the self image of the diffraction grating 60 is obtained as an interference pattern on the image pickup element 70:

$$\frac{Z_0 Z}{Z_0 - Z} = \frac{md^2}{\lambda} \qquad \text{Expression 2}$$

Here, Z is a distance from the diffraction grating 60 to the image pickup element 70, which is referred to as a Talbot distance. In addition, m is a natural number, d is a grating pitch of the diffraction grating 60, and $Z_0$ is a distance from the diffraction grating 60 to an image plane of the test object 50. Assume that a direction from the diffraction grating 60 to the image pickup element 70 is positive. The grating pitch d of the diffraction grating 60 is determined in accordance with a magnitude of the aberration of the test object 50 and a pixel size of the image pickup element 70.

Figure 2:
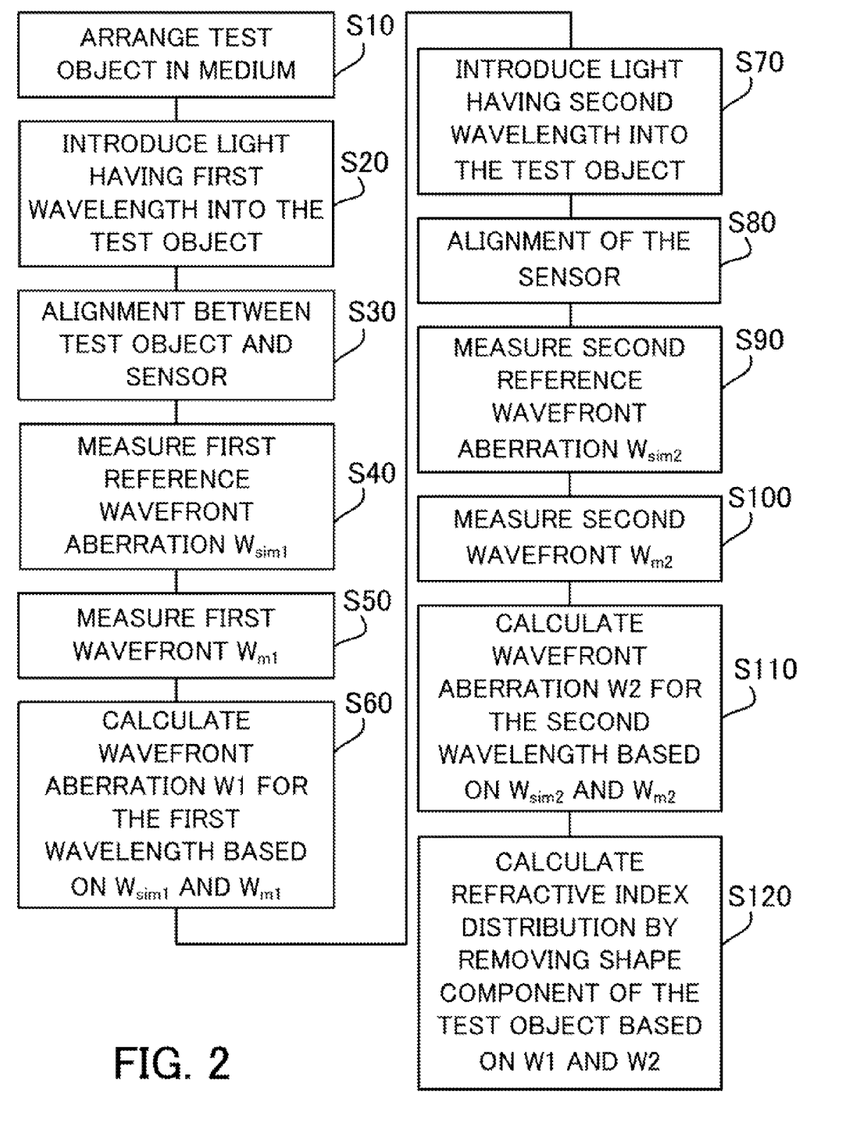
FIG. 2 is a flowchart for illustrating a processing procedure of a refractive index distribution according to the first embodiment.

FIG. 2 is a flowchart for illustrating a processing procedure of calculating the internal refractive index distribution of the test object 50, and "S" stands for the step. The calculating processing is executed as a computer program by an operation unit 80 (processor), such as a microcomputer illustrated in FIG. 1.

Initially, as illustrated in FIGS. 1A and 1B, a medium M is filled in the test object case 51 and the test object 50 is arranged in the medium (S10).

Next, light having a first wavelength is introduced into the test object 50 (S20). In measuring a transmitted wavefront for the first wavelength, mixing of light having a second wavelength is prevented. This embodiment turns off the light source 11 or inserts a shutter, etc. between the light source 11 and the beam splitter 20. Alternatively, a wavelength-selective filter etc. configured to shield the light having the second wavelength may be inserted into a space between the beam splitter 20 and the pinhole 30.

Then, the test object 50, the diffraction grating 60, and the image pickup element 70 are arranged in place (S30). The diffraction grating 60 and the image pickup element 70 are referred collectively to as a sensor. The NA on the image side is reduced by changing an interval between the pinhole 30 and the test object 50 in the optical axis direction. In order to obtain the diffraction grating 60's self image on the overall surface of the image pickup element 70 in the Talbot interferometer, it is necessary to restrain the NA down to 0.3 or smaller. When the light receiving surface of the sensor is smaller than the diameter of the light flux that has transmitted the test object 50, the light can fall within the light receiving surface by separating the sensor from the test object 50. Decentering and inclining of the test object 50 are also adjusted.

Next, a simulation wavefront $W_{sim1}$ of a reference object having a known shape and a known refractive index distribution is calculated (S40). The simulation wavefront $W_{sim1}$ is a first reference transmitted wavefront for the first wavelength and the corresponding medium. This step supposes the reference object has the same shape as the test object 50 and a uniform specific refractive index distribution, and separately calculates a (reference) transmitted wavefront in the same arrangement as that of S30. The same shape as the test object 50 means a designed value of the test object 50. Instead of the simulation, the reference object which has the same shape as the test object 50 but does not have a homogeneous refractive index distribution may be actually produced, and the transmitted wavefront may be actually measured in the measuring apparatus illustrated in FIG. 1.

Figure 3A:
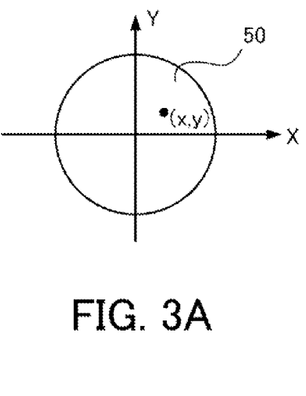
FIGS. 3A and 3B are diagram illustrating a coordinate system defined on a test object and an optical path of a ray in the measuring unit according to the first embodiment.

Expression 3 expresses a first reference transmission wavefront $W_{sim1}$ at a point (x, y) in the test object 50 illustrated in FIG. 3A. A coordinate (0, 0) in FIG. 3A is the center coordinate of the test object 50, and corresponds to a point on the optical axis. In order to simplify Expression 3, a thickness of a side surface of the test object case 51 is ignored.

$$W_{sim1}\{L_{1a}(x,y)+n_1L_{1b}(x,y)+N_1(0,0)L_1(x,y)+n_1L_{1c}(x,y)+L_{1d}(x,y)\}-\{L_{1a}(0,0)+n_1L_{1b}(0,0)+N_1(0,0)L_1(x,y)+n_1L_{1c}(0,0)+L_{1d}(0,0)\} \qquad \text{expression 3}$$

Figure 3B:
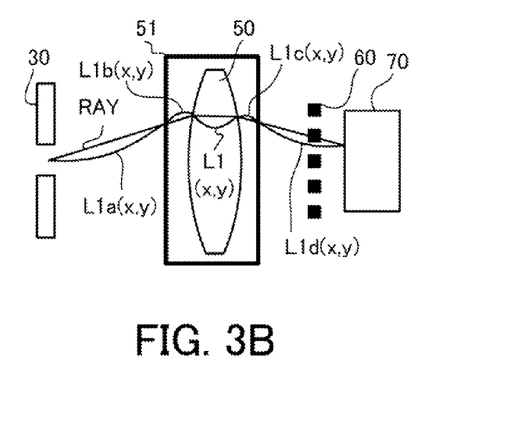

$L_{1a}(x, y)$, $L_{1b}(x, y)$, $L_{1c}(x, y)$, and $L_{1d}(x, y)$ are geometric distances among components along the ray illustrated in FIG. 3B. The ray illustrated in FIG. 3B means a ray that passes a certain point (x, y) inside the test object 50 illustrated in FIG. 3A. $L_1(x, y)$ is a geometric length of an optical path of a ray in the test object 50 or a thickness of the test object along the ray. $L_1(x, y)$ can be calculated by ray tracing using the reference object. In calculating the first reference transmitted wavefront $W_{sim1}$, $L_1(x, y)$ at an arbitrary point may also be calculated.

Assume $n_1$ is a refractive index of the medium M for the first wavelength. $N_1(0, 0)$ is a refractive index of the reference object for the first wavelength. $N_1(0, 0)$ corresponds to a refractive index made by averaging in the optical axis direction the refractive index at the center coordinate (0, 0) of the test object 50 illustrated in FIG. 3A. It is necessary to obtain $n_1(0, 0)$ of the test object 50 using another measuring method, such as a refractive index measuring method using the low coherence interferometry.

Next, as illustrated in FIG. 1A, the (first) transmitted wavefront $W_{m1}$ of the test object 50 is measured for the first wavelength (S50). This step includes obtaining an image of an interference pattern of the image pickup element 70, and image restoration processing of a transmitted wavefront by a processor (not illustrated). The image restoration processing of the transmitted wavefront ("wavefront restoration" hereinafter) utilizes the fast Fourier transform ("FFT") method.

The wavefront restoration by the FFT method is a method that separates a carrier from the aberration using a characteristic in which the aberration disturbs the carrier pattern of the interference pattern. More specifically, the two-dimensional FFT is performed for the interference pattern, and the interference pattern is converted into the frequency map. Next, the inverse fast Fourier transform (iFFT) method is performed after only part near the carrier frequency is picked up in the frequency map and a coordinate is transformed so as to set the carrier frequency to the origin. Thereby, a phase term of the complex amplitude is found. The resultant phase map becomes the transmitted wavefront.

The first transmitted wavefront $W_{m1}$ is expressed by Expression 4 using a geometric distance illustrated in FIG. 3B:

$$W_{m1} = \{L_{1a}(x,y) + n_1 L_{1b}(x,y) + N_1(x,y)[L_1(x,y) + dL(x,y)] + n_1[L_{1c}(x,y) - dL(x,y)] + L_{1d}(x,y)\} - \{L_{1a}(0,0) + n_1 L_{1b}(0,0) + N_1(0,0)[L_1(0,0) + dL(0,0)] + n_1[L_{1c}(0,0) - dL(0,0)]L_{1d}(0,0)\}$$

Expression 4

$N_1(x, y)$ means a refractive index averaged in a traveling direction of a ray illustrated in FIG. 3B. $dL(x, y)$ is a thickness error (shape error) from a designed value of the test object 50 in the ray traveling direction. $L_{1a}(x, y)$, $L_{1b}(x, y)$, $L_{1c}(x, y)$, $L_{1d}(x, y)$ and $L_1(x, y)$ have the same value in Expressions 3 and 4. This is because a difference of the optical path is negligibly small between a case where there is a refractive index distribution and a case where there is no refractive index distribution.

The (first) wavefront aberration $W_1$ corresponding to a difference between the first reference transmitted wavefront $W_{sim1}$ found in S40 and the first transmitted wavefront $W_{m1}$ found in S50 can be calculated as in Expression 5:

$$W_{m1} - W_{sim1} = [N_1(x,y) - N_1(0,0)]L_1(x,y) + [N_1(x,y) - n_1]dL(x,y) - [N_1(0,0) - n_1]dL(0,0)$$

Expression 5

Next, an approximation of Expression 6 enables the wavefront aberration $W_1$ for the first wavelength to be calculated (S60). Expression 7 defines a relationship between the wavefront aberration $W_1$ and the refractive index distribution $GI_1$ for the first wavelength:

$$[N_1(x,y) - N_1(0,0)]dL(x,y) \sim 0$$

Expression 6

$$W_1 = GI_1 \cdot L_1(x,y) + [N_1(0,0) - n_1]dL(x,y) - [N_1(0,0) - n_1]dL(0,0) \quad GI_1 = N_1(x,y) - N_1(0,0)$$

Expression 7

The measurement result of the transmitted wavefront $W_{m1}$ obtained in S50 contains a refractive index distribution of the test object 50, influence of the test object shape, influence of the test object shape error, and an offset by the measuring system. Among them, the influence of the test object shape and the offset by the measuring system are cancelled out by subtracting the reference transmitted wavefront $W_{sim1}$ from the transmitted wavefront $W_{m1}$. As a result, S60 finds the wavefront aberration $W_1$, and obtains remaining information of the refractive index distribution of the test object 50 and the influence of the test object shape error.

Next, light having a second wavelength is introduced into the test object 50, as illustrated in FIG. 1B (S70). In measuring a transmitted wavefront for the second wavelength, mixing of light having the first wavelength is prevented. This embodiment turns off the light source 10 or inserts a shutter, etc. between the light source 10 and the beam splitter 20. Alternatively, a wavelength-selective filter etc. configured to shield the light having the first wavelength may be inserted into a space between the beam splitter 20 and the pinhole 30.

Then, the sensor position is adjusted (S80). As illustrated in Expression 2, the Talbot distance changes as the wavelength changes. Thus, the positions of the diffraction grating 60 and the image pickup element 70 are changed into proper positions.

According to the same procedure as that for the first wavelength, the wavefront aberration $W_2$ is found for the second wavelength. In other words, initially, a simulation wavefront $W_{sim2}$ of the reference object for the second wavelength is calculated (S90). The simulation wavefront $W_{sim2}$ is referred to as a second reference transmitted wavefront obtained by a measurement using the second wavelength. Next, the (second) transmitted wavefront $W_{m2}$ of the test object 50 is measured for the second wavelength (S100). Finally, a (second) wavefront aberration $W_2$ is found which corresponds to a difference between the second reference transmitted wavefront $W_{sim2}$ and the second transmitted wavefront $W_{m2}$ (S110). Expression 8 provides a relationship between the wavefront aberration $W_2$ and the refractive index distribution $GI_2$ for the second wavelength:

$$W_2 = GI_2 \cdot L_2(x,y) + [N_2(0,0) - n_2]dL(x,y) - [N_2(0,0) - n_2]dL(0,0) \quad GI_2 N_2(x,y) - N_2(0,0)$$

Expression 8

Assume $n_2$ in Expression 8 is a refractive index of the medium M for the second wavelength. $N_2(x, y)$ is a refractive index made by averaging the refractive index in the traveling direction of the ray that passes the coordinate $(x, y)$ in the test object 50. Similar to $N_1(0, 0)$, $N_2(0, 0)$ is a refractive index which may be obtained by using another measuring method.

$L_2(x, y)$ is a geometric length of an optical path of a ray that passes the coordinate $(x, y)$ for the second wavelength or a thickness of the test object 50 along the ray. $L_2(x, y)$ can be calculated by ray tracing when the second reference transmitted wavefront $W_{sim2}$ is calculated. Due to the influence of the chromatic aberration, $L_1(x, y)$ is slightly different from $L_2(x, y)$. On the other hand, since $dL(x, y)$ is much smaller than $L_1(x, y)$ and $L_2(x, y)$, the same value may be used for the first wavelength and the second wavelength.

The wavelength dependency of the refractive index at the coordinate $(x, y)$ in the test object 50 distributes along with the refractive index distribution. $N_1(x, y)$ and $N_2(x, y)$ are related by Expression 9 as an approximation expression.

$$N_2(x, y) - N_1(x, y) = \frac{1}{A}[N_2(x, y) - 1]$$

$$A = \frac{N_{02} - 1}{N_{02} - N_{01}}$$

Expression 9

$N_{01}$ and $N_{02}$ are refractive indices (literature values) of the glass material for each of the first and second wavelengths before molding. These refractive indices may use separately measured $N_1(0, 0)$ and $N_2(0, 0)$ instead of the literature values. Strictly speaking, $N_1(x, y)$, $N_2(x, y)$, $N_{01}$, and $N_{02}$ in Expression 9 use the (absolute) refractive indices to vacuum but the air's refractive index is about 1 and thus the (relative) refractive index relative to air may be used instead of the absolute refractive index.

Using Expression 9, Expression 10 correlates the refractive index distribution $GI_1$ for the first wavelength with the refractive index distribution $GI_2$ for the second wavelength:

$$GI_2 = \frac{N_{02} - 1}{N_{01} - 1} GI_1$$

Expression 10

The shape error $dL(x, y)$ of the test object 50 is removed based on the wavefront aberration $W_1$ for the first wavelength of Expression 7 and the wavefront aberration $W_2$ for the second wavelength of Expression 8. Expression 11 can be led out of Expression 10 which is used to extract the internal refractive index distribution $GI_1$ of the test object 50 for the first wavelength:

$$GI_1 = \frac{(N_1(0,0)-n_1)W_2 - (N_2(0,0)-n_2)W_1}{\frac{N_{02}-1}{N_{01}-1}[N_1(0,0)-n_1] - [N_2(0,0)-n_2]} \cdot \frac{1}{L_{eff}(x,y)}$$ Expression 11

$$L_{eff}(x,y) = \frac{(N_{02}-1)(N_1(0,0)-n_1)L_2(x,y) - (N_{01}-1)(N_2(0,0)-n_2)L_1(x,y)}{(N_{02}-1)(N_1(0,0)-n_1) - (N_{01}-1)(N_2(0,0)-n_2)}$$

$L_{eff}(x, y)$ is an effective thickness of the test object 50 obtained from $L_1(x, y)$ and $L_2(x, y)$. When $L_2(x, y)$ is equal to $L_1(x, y)$, or when the ray traveling directions are equal to each other for the first and second wavelengths, $L_{eff}(x, y)$ is equal to $L_1(x, y)$ and $L_2(x, y)$.

Finally, the refractive index distribution $GI_1$ of the test object 50 for the first wavelength is calculated by substituting the wavefront aberration $W_1$ for the first wavelength, the wavefront aberration $W_2$ for the second wavelength, and the effective thickness $L_{eff}(x, y)$ for Expression 11 and by removing the shape component (S120). The shape component is the influence of the shape error of the test object, and corresponds to a sum of the effective thickness $L_{eff}(x, y)$ obtained from the designed value of the test object 50 and the shape error $dL(x, y)$ from the designed value of the test object 50. When the internal refractive index distribution $GI_2$ of the test object 50 for the second wavelength is to be calculated, the calculated $GI_1$ may be substituted for Expression 10.

The refractive index of the medium M is necessary to calculate the first reference transmitted wavefront $W_{sim1}$ in S40, the second reference transmitted wavefront $W_{sim2}$ in S90, the internal refractive index distribution $GI_1$ of the test object 50 using Expression 11. The refractive index of the medium M may be calculated by using a relationship between the refractive index and the temperature (literature values) or may be separately measured by using the low coherence interferometry, etc.

When it is calculated by using the relationship between the refractive index and the temperature, the temperature of the medium M may be measured by a thermometer, etc. when the first transmitted wavefront $W_{m1}$ and the second transmitted wavefront $W_{m2}$ are measured (S50, S100).

The refractive index of the medium M can be measured by using an element having a known refractive index that is approximately similar to that of the medium M and a wedge shape, such as a glass prism. More specifically, the prism is immersed in the medium, and the wavefront is measured for each of the light having the first wavelength and the light having the second wavelength, and the refractive index of the medium M may be calculated based on information of an inclination and shape of the wavefront.

While this embodiment uses oil for the medium M, water or ethanol may be used for measurements. The medium M may be gaseous or solid for measurements. When the medium M is a gas, the refractive index in Expression 9 may use the absolute refractive index. When the refractive index of the medium M has a distribution, the precision of the refractive index distribution of the test object 50 lowers. Therefore, the medium M having a uniform refractive index distribution may be used.

In the refractive index distribution measuring method of this embodiment, a relationship between the refractive index of the test object 50 and the refractive index of the medium M for each of the first wavelength and the second wavelength greatly affects the measurement precision of the refractive index distribution to be calculated. Accordingly, when the wavefront aberration $W_1$ for the first wavelength contains an error $\delta W_1$ and the wavefront aberration $W_2$ for the second wavelength contains an error $\delta W_2$, an error of the calculated refractive index distribution $GI_1$ is considered. For simplicity purposes, assume that the error of the wavefront aberration for the first wavelength and the error of the wavefront aberration for the second wavelength are independent and $\delta W_1 = \delta W_2 = \delta W$ is established. Expression 12 provides a relationship between an error $\delta W_{GI1}$ of the wavefront aberration $W_{GI1}$ ($=GI_1 \times L_{eff}(x,y)$) and the error $\delta W$.

$$\delta W_{GI1} = \frac{\sqrt{(N_1(0,0)-n_1)^2 + (N_2(0,0)-n_2)^2}}{\frac{N_{02}-1}{N_{01}-1}[N_1(0,0)-n_1] - [N_2(0,0)-n_2]} \delta W$$ Expression 12

For example, assume that $N_1(0,0)=N_{01}=1.80$, $N_2(0,0)=N_{02}=1.83$, $n_1=1.70$, $n_2=1.75$, $\delta W=0.1\%$, then $\delta W_{GI1}$ becomes 0.5%.

In order to reduce the error $\delta W_{GI1}$, the numerator of the coefficient of $\delta W$ may be made smaller and denominator of the coefficient may be made larger in Expression 12. As a guide of the reduction of the error $\delta W_{GI1}$, the medium M may be selected in such a way that a refractive index difference between the test object 50 and the medium M can be smaller and the wavelength dependency of the refractive index of each of the test object 50 and the medium M can greatly differ from each other. In addition, a difference between the first wavelength and the second wavelength may be maintained large so that a difference of the wavelength dependency of the refractive index can stand out.

A large aberration caused by a refractive index difference between the test object and the medium M can be measured by using the Talbot interferometer for the measuring unit as in this embodiment. The Talbot interferometer is one type of a lateral shearing interferometer configured to measure as an interference pattern a difference between the transmitted wavefront and its sheared transmitted wavefront.

The shearing interferometer is a measuring unit configured to find an amount corresponding to a gradient of a wavefront shape of a transmitted wavefront. A lateral shift amount of the transmitted wavefront is referred to as a shear amount, and a ratio of the shear amount to the diameter of the light is referred to as a shear ratio. By reducing the shear ratio, a large transmitted wavefront aberration can be measured as a small aberration (shear wavefront) that does not make dense the interference pattern.

In general, when the shear ratio is excessively small in the shearing interferometer, the shear wavefront is embedded in noises and the precision deteriorates. Thus, the shear ratio may be 3 to 5% as large as the diameter of the pupil. However, this embodiment sets the shear ratio to 1.5% or smaller, e.g., about 0.3 to 1.5% so as to measure the transmitted wavefront having a large aberration with a small shear wavefront.

The shear ratio can be expressed as in Expression 13 using Expression 2 where D is a diameter of the light flux on the image pickup element 70, and $D_0$ is a diameter of the light flux on the diffraction grating 60:

$$\text{Shear Ratio} = \frac{\lambda Z}{dD} = \frac{md}{D_0} \qquad \text{EXPRESSION 13}$$

From Expression 13 the shear ratio is proportional to the grating pitch d of the diffraction grating 60, and from Expression 2 the pitch of the diffraction grating 60 affects the Talbot distance Z. It is thus necessary to determine the pitch so as to prevent interference among the components in the measuring apparatus. For example, if it is assumed that $D_0$ is about 10 mm when m=1, the grating pitch may be about 30 to 150 μm.

While this embodiment discusses use of the Talbot interferometer, a lateral shearing interferometer, a lateral shearing interferometer, a radial shearing interferometer, and another shearing interferometer different from the Talbot interferometer may be used.

In addition to the shearing interferometer, any measuring units may be used as long as the measuring unit can detect a gradient or inclination of the wavefront as a measurable physical amount, even when the transmitted wavefront has a large aberration. For example, the measuring unit may use the Hartman method, the Shack-Hartman method, or the Ronchi test.

For instance, the Shack-Hartman sensor is configured to condense light incident upon a lens array upon a CCD. When the inclined transmitted wavefront enters the lens array, the position of the condensing point shifts on the CCD. Since the Shack-Hartman sensor converts an inclination of a transmitted wavefront into a positional shift of a condensing point and measures it, the Shack-Hartman sensor can measure a wavefront having a large aberration.

When the Shack-Hartman sensor is used to measure the first transmitted wavefront $W_{m1}$ and the second transmitted wavefront $W_{m2}$, the arrangement of the measuring unit may be identical. Hence, when the first transmitted wavefront $W_{m1}$ has an error $\delta W$, the wavefront aberration $W_{m2}$ for the second wavelength may also have an error (aberration) $\delta W$ of a similar amount and a similar type.

Since a value of $N_1(0, 0)-n_1$ is close to a value of $N_2(0, 0)-n_2$ in the refractive index distribution measuring method of this embodiment, there is a cancelling effect of the error $\delta W$ to some extent when the error $\delta W$ is substituted for Expression 11. The measuring unit is less affected by the arrangement errors of the optical elements in the measurement unit, and can provide a precise measurement.

This embodiment utilizes two types of light sources so as to emit the light having the first wavelength and the light having the second wavelength. However, beams of the two types of wavelengths may be obtained from the same light source having a variable wavelength, such as a semiconductor laser or the beams of the two types of wavelengths may be generated using a broadband light source, such as a Supercontinuum light source, and a narrowband filter. Since the shearing interferometer or the Hartman method is used, an incoherent light source, such as a Halogen lamp, may be used for the broadband light source.

As discussed above, the refractive index distribution measuring method of this embodiment immerses the test object in the medium M, switches the wavelength, and measures the first transmitted wavefront and the second transmitted wavefront. This operation needs only simple switching of the wavelength and does not require the adjustment of the refractive index of the medium. Moreover, since working of the test object is unnecessary, the measurement time period is shortened. Furthermore, no change of the refractive index distribution occurs because the test object is not worked. Therefore, the refractive index distribution measuring method of this embodiment can precisely and quickly measure the internal refractive index distribution of the test object in the nondestructive state.

Second Embodiment

In a second embodiment, a measuring unit other than the interferometer is used for measurements of a test object having a negative power. Those elements in this embodiment, which are the corresponding elements in the first embodiment, will be designated by the same reference numerals.

Figure 4:
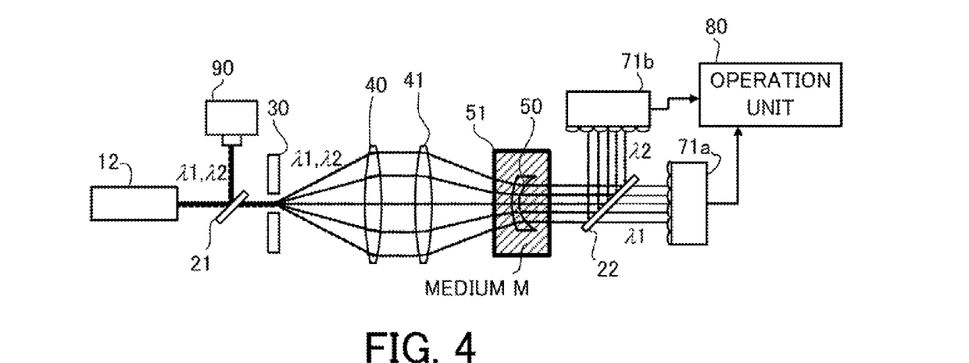
FIG. 4 is a block diagram of a refractive index distribution measuring apparatus according to a second embodiment.

FIG. 4 is a block diagram of a measuring apparatus of this embodiment. The test object 50 is a lens (optical element) having a negative power. The medium M filled in a space around the test object 50 is, for example, water (although FIG. 4 illustrates it as a medium).

A light source 12 is configured to simultaneously emit beams of two types of wavelengths, such as a multimode oscillating laser (e.g., a fundamental wave and a second harmonic of a YAG laser) or a combination of a broadband light source (e.g., a Supercontinuum light source) and a specific wavelength-selective filter. Shack-Hartman sensors 71$a$, 71$b$ are used to measure transmitted wavefronts.

The light having the first wavelength $\lambda_1$ and the light having the second wavelength $\lambda_2$ emitted from the light source 12 are split by the beam splitter 21, such as a half-mirror, into a transmitting beam and a reflected beam. The light reflected by the beam splitter 21 is received by the wavemeter 90, such as a spectrometer and a light spectrum analyzer. The wavemeter 90 precisely specifies the first wavelength $\lambda_1$ and the second wavelength $\lambda_2$. Here, an optical axis direction is a direction in which the light from the light source 12 travels, and an optical axis is the center of the light flux.

The light that has transmitted the beam splitter 21 becomes an ideal spherical wave when it passes the pinhole 30. The light having the first wavelength $\lambda_1$ and the light having the second wavelength $\lambda_2$ are converted into convergent light via collimator lenses 40 and 41. A lens, such as an achromatic lens, in which the chromatic aberration has been corrected to some extent may be used for each of the collimator lenses 40 and 41. The convergent light passes water in the test object case 51, and enters the test object 50. The light that has transmitted through the test object 50 becomes approximately parallel light, passes water, and goes out of the test object case 51 through water.

The light having the first wavelength $\lambda_1$ transmits the beam splitter 22, such as a dichroic mirror, and is measured by the Shack-Hartman sensor 71$a$. The light having the second wavelength $\lambda_2$ is reflected on the beam splitter 22, and measured by the Shack-Hartman sensor 71$b$.

The operation unit 80 calculates the internal refractive index distribution of the test object 50 based on the images taken by the Shack-Hartman sensors 71$a$, 71$b$.

In comparison with the Talbot interferometer, the Shack-Hartman sensor requires the NA of the light flux incident upon the sensor to be strictly controlled. However, the Shack-Hartman sensor makes easier the alignment because it is unnecessary to secure the Talbot distance, and the Shack-Hartman sensor can provide a quick measurement.

This embodiment utilizes two Shack-Hartman sensors, and simultaneously measure the first transmitted wavefront $W_{m1}$ and the second transmitted wavefront $W_{m2}$. Instead, when a single Shack-Hartman sensor is used, a wavelength-selective filter, etc. may be inserted and ejected for measurements twice instead of using the beam splitter 22. The wavelength-selective filter may be arranged in front of the Shack-Hartman sensor 71*a* or between the light source 12 and the pinhole 30.

Next follows a calculating procedure of the internal refractive index distribution of the test object 50 according to this embodiment. Initially, as illustrated in FIG. 4, water is filled in the space around the test object 50 (S10). Next, the light having the first wavelength $\lambda_1$ and the light the second wavelength $\lambda_2$ are simultaneously introduced into the test object (S20 and S70). Then, decentering and inclining of the test object 50 are performed relative to the optical axis.

In addition, a position of the test object in the optical axis direction is adjusted so as to turn the transmitting light into approximately parallel light (S30). An adjustment to collimate the transmitting light may be performed by changing the collimator lens 41 into a lens having a proper NA instead of the adjustment of the position of the test object 50. Unlike the Talbot interferometer, it is unnecessary to adjust the positions of the Shack-Hartman sensors 71*a*, 71*b*.

Then, the wavefront aberration $W_1$ for the first wavelength and the wavefront aberration $W_2$ for the second wavelength are found by the procedure similar to that of the first embodiment (S60 and S110). Since this embodiment uses the Shack-Hartman sensor, the operation of S80 (positional adjustment of the sensor) is unnecessary. Since the first transmitted wavefront $W_{m1}$ and the second transmitted wavefront $W_{m2}$ are simultaneously measured by using the Shack-Hartman sensors 71*a*, 71*b*, S40 to S60 and S90 to S110 can be simultaneously performed.

Finally, Expression 11 is used to calculate the internal refractive index distribution of the test object (S120).

Third Embodiment

A third embodiment discusses a refractive index distribution measuring apparatus that can omit decentering, inclining, and adjusting a position in the optical axis direction of the test object, which are necessary for the first and second embodiments. Those elements in this embodiment, which are the same as corresponding elements in the first and second embodiments, are designated by the same reference numerals.

Figure 5:
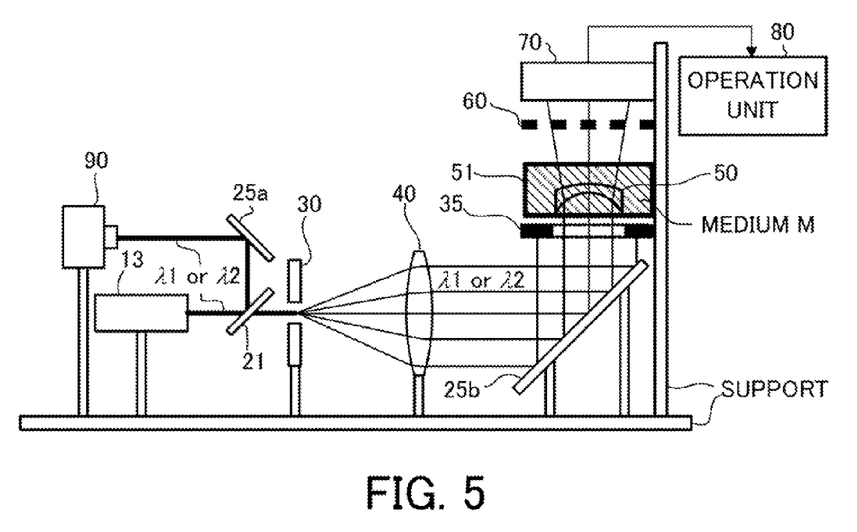
FIG. 5 is a block diagram of a refractive index distribution measuring apparatus according to a third embodiment.

FIG. 5 is a block diagram of a measuring apparatus of this embodiment. The test object 50 is a lens (optical element) having a negative power. The medium M filled in a space around the test object 50 is, for example, oil. A light source 13 is a light source configured to emit beams of two or more wavelengths at proper timings, such as a wavelength variable laser (e.g., a semiconductor laser) or a combination of a broadband light source (e.g., a Halogen lamp) and a specific wavelength-selective filter. A Talbot interferometer is used to measure a transmitted wavefront. Each optical element is fixed onto a support, such as a rack or a rail.

Light having a first wavelength $\lambda_1$ (or a second wavelength $\lambda_2$) emitted from the light source 13 is split into transmitting light and reflected light by the beam splitter 21. The light reflected on the beam splitter 21 is reflected on the mirror 25*a*, such as an aluminum mirror, and received by the wavemeter 90. The wavemeter 90 precisely specifies the first wavelength $\lambda_1$ (or the second wavelength $\lambda_2$). Here, the optical axis direction is a direction in which the light from the light source 13 is emitted, and the optical axis is a center of the light flux.

The light that has transmitted through the beam splitter 21 becomes an ideal spherical wave after it passes the pinhole 30. The divergent light is turned into parallel light by the collimator lens 40, and reflected on a plane mirror 25*b* perpendicularly upwardly. The optical axis is also deflected perpendicularly upwardly.

Unnecessary light in the parallel light is shielded by a stop 35, such as a diaphragm, and necessary light enters the test object 50 via oil in the test object case 51. The light that has transmitted the test object becomes divergent light, and is measured by the Talbot interferometer that includes the diffraction grating 60 and the image pickup element 70. The bottom surface of the test object case 51 may be configured perpendicular to the optical axis.

Next follows a calculating procedure of the refractive index distribution of the test object 50 according to this embodiment. Initially, as illustrated in FIG. 5, the test object 50 is immersed into oil (S10). Next, the light having the first wavelength $\lambda_1$ is emitted from the light source 13 (S20). When the broadband light source is used, the narrowband filter that allows the light having the first wavelength $\lambda_1$ to transmit may be inserted between the light source 13 and the beam splitter 21.

Next, the sensor position and the Talbot distance are adjusted (S30). The bottom surface of the test object case 51 is perpendicular to the optical axis, and the light incident upon the test object 50 is parallel light. Therefore, decentering, inclining, and adjusting of the position in the optical axis direction of the test object are performed only by placing the test object 50 in the test object case 51.

The wavefront aberration $W_1$ for the first wavelength is found by the procedure similar to that of the first embodiment (S40 to S60). Next, the light having the second wavelength $\lambda_2$ is emitted from the light source 13 (S70), the distance is properly adjusted to the Talbot distance (S80), and the wavefront aberration $W_2$ for the second wavelength is found (S90 to S110). Finally, the internal refractive index distribution of the test object 50 is calculated using Expression 11 (S120).

In this embodiment, the plane mirror 25*b* deflects the parallel light perpendicularly upwardly, and the test object 50 is placed in contact with the test object case 51. This configuration can omit decentering, inclining, and adjusting of the position in the optical axis direction of the test object. Instead of deflecting the parallel light perpendicularly upwardly, the parallel light may be deflected perpendicularly downwardly, and the stop 35, the test object case 51, the test object 50, the diffraction grating 60, and the image pickup element 70 may be arranged on the lower side.

In addition, in order to simplify the calculating process of the internal refractive index distribution of the test object 50, this embodiment shields the unnecessary light (parallel light that has transmitted the medium M) by the stop 35. However, as understood from Expression 2, the parallel light and the divergent light have different Talbot distances. Therefore, the divergent light can be separated from the parallel light without the stop 35.

The measurement result of the refractive index distribution measuring apparatus (refractive index distribution measuring method) according to the first to third embodiments may be fed back to a manufacturing method of an optical element. This method for manufacturing the optical element includes the steps of molding an optical element based on a designed optical element, measuring a shape of the molded optical element, evaluating the shape precision, and evaluating the optical performance of the optical element that satisfies the shape precision. The refractive index distribution measuring method of this embodiment is applicable to the step of evaluating the optical performance. When the evaluated optical performance does not satisfy the required specification, a correction amount of an optical surface of the optical element is calculated and the optical element is redesigned by using the result. When the evaluated optical performance satisfies the required specification, the optical element is mass-produced.

The manufacturing method of the optical element according to this embodiment can precisely measure the internal refractive index distribution of the optical element, and mass-produce the optical element through molding even when it is made of a high refractive index glass material.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-119558, filed on May 25, 2010, which is hereby incorporated by reference herein in its entirety.

INDUSTRIAL APPLICABILITY

The refractive index distribution measuring apparatus is applicable to an application of manufacturing an optical element.

The invention claimed is:

1. A refractive index distribution measuring method comprising the steps of:
   measuring a transmitted wavefront of a test object by introducing reference light into the test object that is arranged in a medium having a refractive index different from a refractive index of the test object; and
   calculating a refractive index distribution of the test object by using a measurement result of the transmitted wavefront,
   wherein the measuring step measures a first transmitted wavefront for a first wavelength and a second transmitted wavefront for a second wavelength different from the first wavelength, and
   wherein the calculating step calculates the refractive index distribution of the test object by removing a shape component of the test object utilizing measurement results of the first and the second transmitted wavefront, and a transmitted wavefront of a reference object arranged in the medium for each of the first and second wavelengths, the reference object having the same shape as the test object and a specific refractive index distribution.

2. The refractive index distribution measuring method according to claim 1, wherein the measuring step uses a shearing interferometer to measure the transmitted wavefront of the object.

3. The refractive index distribution measuring method according to claim 1, wherein the measuring step uses a Hartmann sensor to measure the transmitted wavefront of the object.

4. A production method for an optical element comprising the steps of:
   molding the optical element; and
   evaluating a molded optical element by measuring refractive index distribution of the optical element with a refractive index distribution measuring method, wherein the refractive index distribution measuring method includes the steps of:
   measuring a transmitted wavefront of a test object by introducing reference light into the test object that is arranged in a medium having a refractive index different from a refractive index of the test object; and
   calculating a refractive index distribution of the test object by using a measurement result of the transmitted wavefront,
   wherein the measuring step measures a first transmitted wavefront for a first wavelength and a second transmitted wavefront for a second wavelength different from the first wavelength, and
   wherein the calculating step calculates the refractive index distribution of the test object by removing a shape component of the test object utilizing measurement results of the first and the second transmitted wavefront, and a transmitted wavefront of a reference object arranged in the medium for each of the first and second wavelengths, the reference object having the same shape as the test object and a specific refractive index distribution.

5. A refractive index distribution measuring apparatus comprising:
   a light source configured to emit light having a first wavelength and light having a second wavelength;
   a measuring unit configured to measure a transmitted wavefront of a test object arranged in a medium having refractive index different from that of the test object by using the light from the light source; and
   an operation unit configured to calculate a refractive index distribution of the test object based on a first transmitted wavefront measured for the first wavelength and a second transmitted wavefront measured for the second wavelength,
   wherein the operation unit calculates the refractive index distribution of the test object by removing a shape component of the test object utilizing measurement results of the first and second transmitted wavefronts, and a transmitted wavefront of a reference object arranged in the medium for each of the first and second wavelengths, the reference object having the same shape as that of the test object and a specific refractive index.

6. The refractive index distribution measuring apparatus according to claim 5, wherein the measuring unit includes a shearing interferometer.

7. The refractive index distribution measuring apparatus according to claim 5, wherein the measuring unit includes a Hartmann sensor.

* * * * *